(12) United States Patent
Bendickson

(10) Patent No.: US 9,701,197 B1
(45) Date of Patent: Jul. 11, 2017

(54) POSITIVE ACKNOWLEDGEMENT METHOD THAT INFORMATION IS RECEIVED

(75) Inventor: John G. Bendickson, Vinton, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 297 days.

(21) Appl. No.: 13/240,396

(22) Filed: Sep. 22, 2011

(51) Int. Cl.
*B60K 28/00* (2006.01)
*A61B 5/0484* (2006.01)
*A61B 5/0476* (2006.01)

(52) U.S. Cl.
CPC ............ *B60K 28/00* (2013.01); *A61B 5/0476* (2013.01); *A61B 5/04842* (2013.01)

(58) Field of Classification Search
CPC .................................................. A61B 5/04842
USPC ............... 340/501, 502, 573.1; 600/544, 545
See application file for complete search history.

(56) References Cited

U.S. PATENT DOCUMENTS

| | | | | |
|---|---|---|---|---|
| 4,869,264 A * | 9/1989 | Silberstein | ......... | A61B 5/04842 600/544 |
| 5,414,439 A | 5/1995 | Groves et al. | | |
| 5,568,121 A * | 10/1996 | Lamensdorf | ......... | G08B 25/016 340/502 |
| 6,259,981 B1 * | 7/2001 | Wilcosky | ............ | B60R 16/0232 340/459 |
| 6,873,376 B1 | 3/2005 | Rofe | | |
| 8,503,762 B2 | 8/2013 | Ben Tzvi | | |
| 2008/0030685 A1 * | 2/2008 | Fergason | ............... | A61B 3/113 351/210 |
| 2009/0187114 A1 * | 7/2009 | Morikawa | ............... | G06F 3/015 600/545 |
| 2010/0234752 A1 * | 9/2010 | Sullivan | ............. | A61B 5/04842 600/544 |
| 2010/0317988 A1 * | 12/2010 | Terada | .................... | G06F 3/015 600/544 |
| 2011/0040202 A1 * | 2/2011 | Luo | ..................... | A61B 5/04842 600/544 |
| 2012/0253221 A1 * | 10/2012 | Hamaguchi et al. | ......... | 600/544 |
| 2013/0126618 A1 * | 5/2013 | Gao | .......................... | G06K 7/10 235/469 |
| 2014/0373773 A1 * | 12/2014 | Baker | .................... | B60K 37/02 116/282 |
| 2016/0100084 A1 * | 4/2016 | Schofield | ................ | B60C 23/00 348/148 |

* cited by examiner

*Primary Examiner* — Laura Nguyen
(74) *Attorney, Agent, or Firm* — Angel N. Gerdzhikov; Donna P. Suchy; Daniel M. Barbieri

(57) ABSTRACT

A device for acknowledging warning indicators includes an electro-encephalograph for detecting signals in the midline occipital region of the user's brain, and a display system for displaying flashing indictors having differing flashing frequencies. The electro-encephalograph detects differing signals caused by the differing flashing frequencies whenever the user observes one of the flashing indicators, and the device thereby recognizes that the user has observed the warning indicator.

9 Claims, 6 Drawing Sheets

POSITIVE ACKNOWLEDGEMENT METHOD THAT INFORMATION IS RECEIVED

FIELD OF THE INVENTION

The present invention is directed generally toward warning indicators in a computerized system, and particularly toward acknowledging warning indicators using an electroencephalograph.

BACKGROUND OF THE INVENTION

Modern user interfaces in complex systems often include indicators of failure states or other conditions that require user interaction, or that impart otherwise important information. In a well-designed system, such indicators may appear before user interaction is critical, allowing a user time to assess a situation and determine a course of action. Because indicators may not require immediate action, they are often designed to be minimally intrusive so that a user may continue to operate the system. Unobtrusive indicators may allow a user to continue operations, but a user may also ignore such indicators, or even fail to see them.

A system may address this problem by demanding a user acknowledgment of a particular indicator. Such acknowledgement diverts the user's attention from operating the system and requires some type of interaction. Where a user is performing a complex task, such as flying a jet, any diversion of the user's attention is undesirable.

Consequently, it would be advantageous if a method and apparatus existed that were suitable for acknowledging a user has observed an indicator without diverting the user's attention or demanding a physical interaction.

SUMMARY OF THE INVENTION

Accordingly, the present invention is directed to a novel method and apparatus for acknowledging a user has observed an indicator without diverting the user's attention or demanding a physical interaction.

One embodiment of the present invention includes a computer with a display and a sensing device for sensing the user's brain waves. The display includes a plurality of indicators, each indicator configured to flash at a different frequency from each of the other indicators. The sensing device interprets variations in the user's brains waves caused by the different frequencies of the different indicators to determine that the user has observed the indicator.

Another embodiment of the present invention is a method for determining that a user has observed an indicator. An indicator is activated on a display; the indicator flashing at a certain frequency. A sensing device senses differences in brain waves based on the flashing frequency of the indicator and determines, based on those differences, that the user has observed the indicator.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
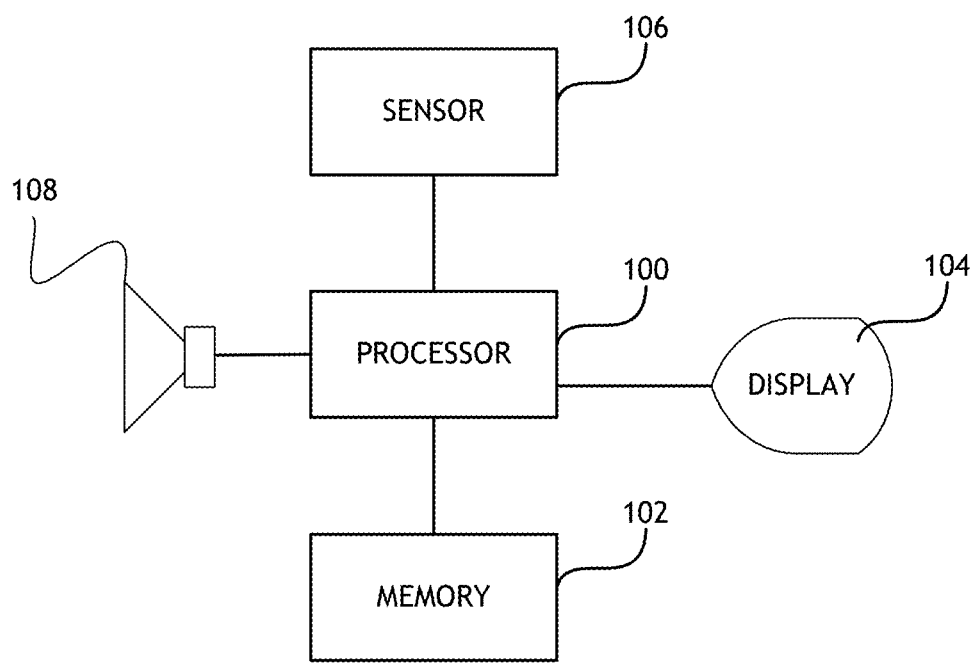
FIG. 1 shows a block diagram of a computer system according to one embodiment of the present invention.

Referring to FIG. 1, a block diagram of an apparatus according to the present invention is shown. The apparatus may include a processor 100 for executing computer code. The processor 100 may be connected to memory 102 for storing the computer code and a display 104. The processor 100 may also be operably connected to a sensor 106 for sensing the brain wave patterns of a user and an audio device 108 for delivering audible messages to the user.

Figure 2:
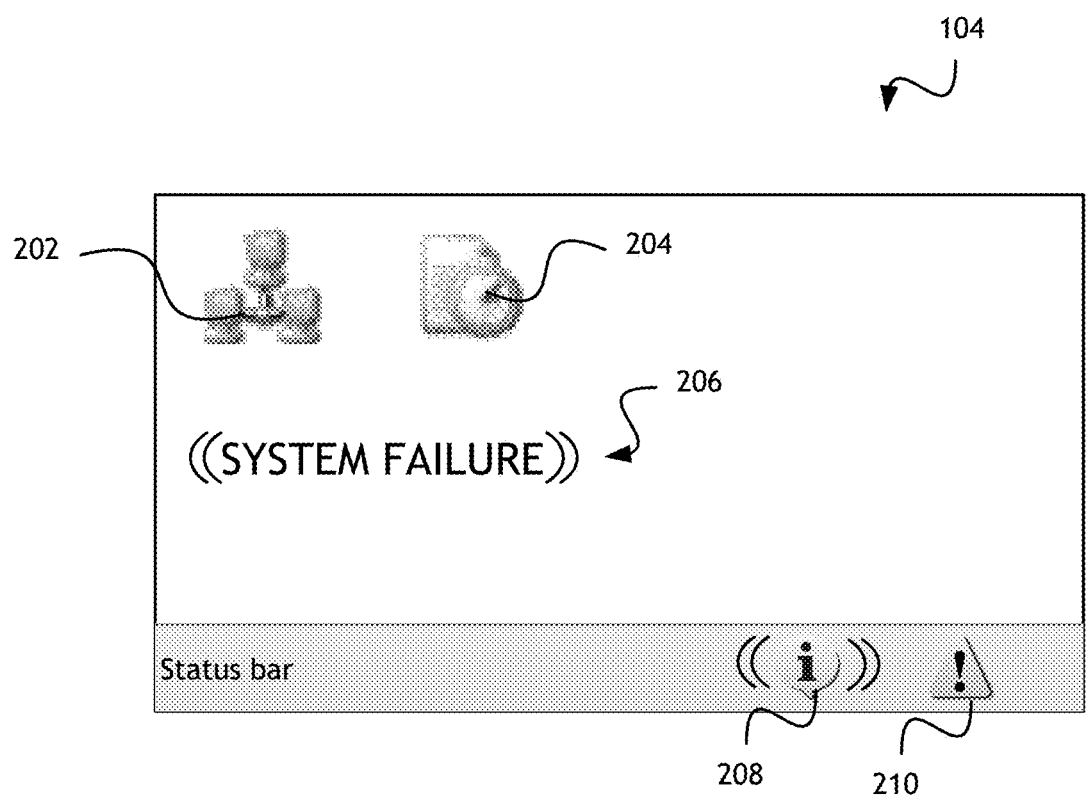
FIG. 2 shows a display implementing one embodiment of the present invention.

Referring to FIG. 2, a representative display 104 implementing the present invention is shown. A display 104 may comprise any mechanism capable of displaying flashing indicators such as a graphic user interface (GUI), a heads-up display (HUD) or a panel of warning lights. The display 104 may include one or more indicators 202, 204, 206, 208, 210, each of the one or more indicators 202, 204, 206, 208, 210 configured to flash. FIG. 2 depicts a plurality of indicators 202, 204, 206, 208, 210, two of the indicators being flashing indicators 206 and 208. In actual application, the flashing of the flashing indicators 206 and 208 may be consciously imperceptible to the user.

The one or more indicators 202, 204, 206, 208, 210 may each be configured to flash at a distinct frequency different from each of the other one or more indicators 202, 204, 206, 208, 210. Two flashing frequencies are distinct when the brain wave patterns of a person observing one flashing frequency are distinguishable from the brain waves patterns of the same person observing the other flashing frequency as brain waves are measured by electro encephalography (EEG).

Research has shown that different frequencies of flashing light result in distinct brain wave patterns in the midline occipital region of the brain, readable by EEG. When an individual observes a certain frequency of flashing light, the individual's brain waves will appear different from the same individual's brain waves when looking at a different frequency of flashing light. That observation is true even when the flashing is consciously imperceptible to the individual. For example, a first indicator may flash at a frequency of nine hertz while a second indicator may flash at a frequency of nine and one quarter hertz. In this example, a frequency differentiation of 0.25 hertz is specified; in practice, any minimum frequency differentiation capable of producing distinguishable brain wave patterns may be used.

A display such as shown in FIG. 2 may have a textual flashing indicator 206 or a graphical flashing indicator 208. By observing the textual flashing indicator 206, a user may generate certain brain wave patterns as compared to when the user is not observing the textual flashing indicator 206. The user's brain wave patterns can be measured and distinguished with EEG. When the user's brain waves, as measured by EEG, indicate that the user is observing the textual flashing indicator 206, the computer utilizing the display 104 may recognize that the user has acknowledged the textual flashing indicator 206. The computer may then perform some acknowledgement response such as recording the user's acknowledgment, beginning resolution of the issue indicated by the textual flashing indicator 206, or clearing the textual flashing indicator 206 so that it no longer occupies the user's field of vision. Conversely, the computer utilizing the display 104 may recognize that the user has not observed the textual flashing indicator 206 for an extended period of time. The computer may then perform some escalation response to ensure that the user is aware of the issue indicated by the textual flashing indicator 206. An escalation response may include making the flashing of the textual flashing indicator 206 consciously intrusive, or delivering an audible warning through the audio device 108.

Where a display includes a second flashing indicator, such as the graphical flashing indicator 208 shown in FIG. 2, each of the two flashing indicators 206 and 208 may flash at a distinct frequency. Based on the differences in the user's brain wave patterns, a computer utilizing the display 104 may determine which of the two flashing indicators 206 and 208 the user is observing and perform various responses. For example, if the computer determines that the user is observing the graphical flashing indicator 208, the computer may perform an acknowledgment response associated with the graphical flashing indicator 208. The computer may also perform an escalation response associated with the textual flashing indicator 206 if the computer determines that the user has not observed the textual flashing indicator 206 during a predetermined period of time.

Another embodiment of the present invention may include a display 104 with one or more flashing indicators to monitor a user's alertness. In this embodiment, a flashing indicator 208 may flash continuously. A computer utilizing such a display 104 may sense the user's brain wave patterns to ensure that the user is observing the flashing indicator 208 at regular intervals. The flashing indicator 208 may be incorporated into an instrument normally utilized by a user such as a speedometer in a car. If the computer determines that the user has not observed the flashing indicator 208 for some predetermined period of time, the computer may perform a warning response such as delivering an audible warning through the audio device 108 indicating that the user may not be alert.

Figure 3:
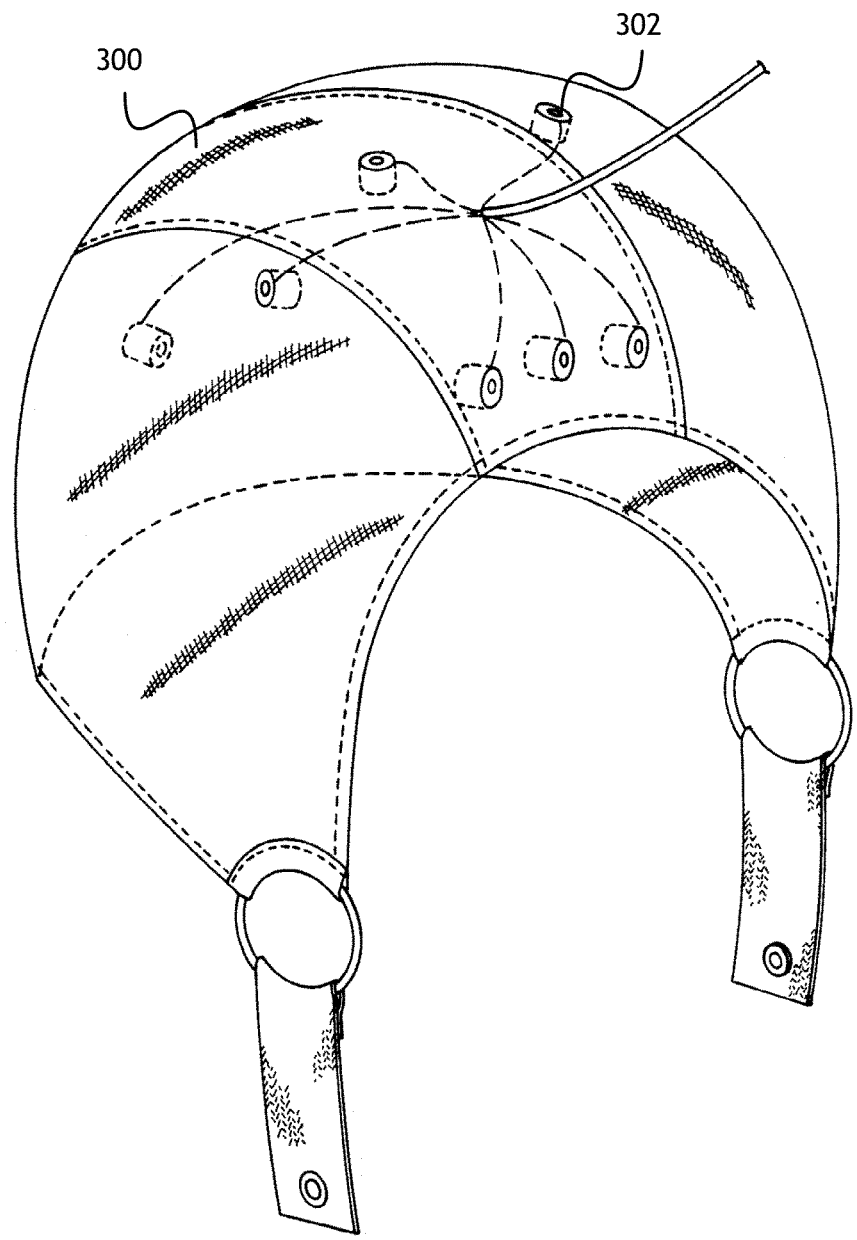
FIG. 3 shows a brain wave sensing apparatus useful for implementing embodiments of the present invention.
Figure 4:
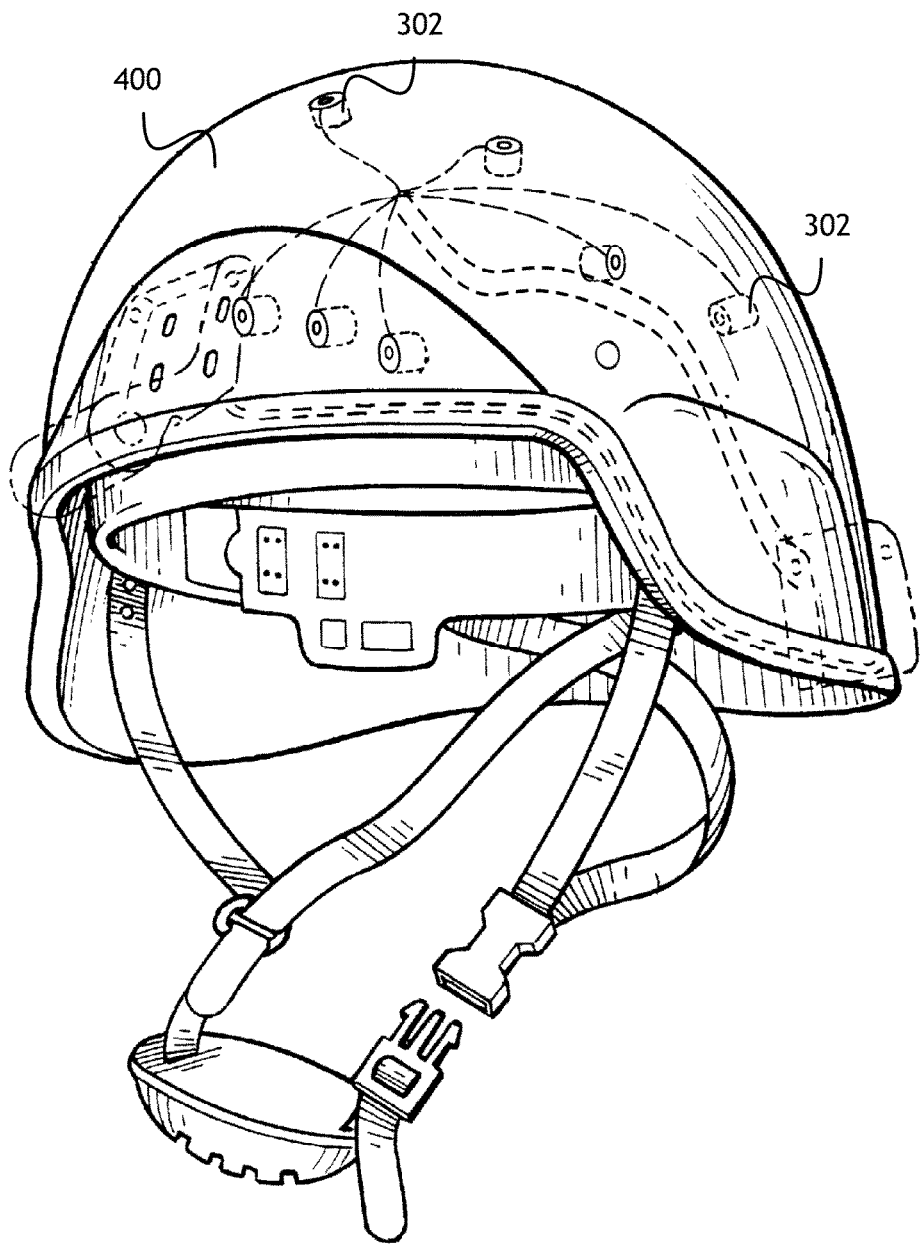
FIG. 4 shows a helmet incorporating brain wave sensors useful for implementing embodiments of the present invention.

Embodiments of the present invention may utilize an EEG sensor such as depicted in FIG. 3. An EEG sensor 106 generally comprises a plurality of electrodes 302 capable of detecting electrical activity in a persons brain when placed at certain specific points on the person's head. Each electrode 302 may be individually positioned or incorporated into a cap 300 at specific locations such that each electrode 302 may be in relatively the same location whenever a person puts on the cap 300. Each electrode 302 may be connected to a processor 100 that may interpret data received from each electrode 302 to determine if the user is observing a flashing indicator. Referring to FIG. 4, electrodes 302 may be incorporated into a helmet 400, such that the electrodes 302 may contact the user's head. In such an implementation, the plurality of electrodes 302 may form an EEG sensor 106 connected to a processor 100.

Figure 5:
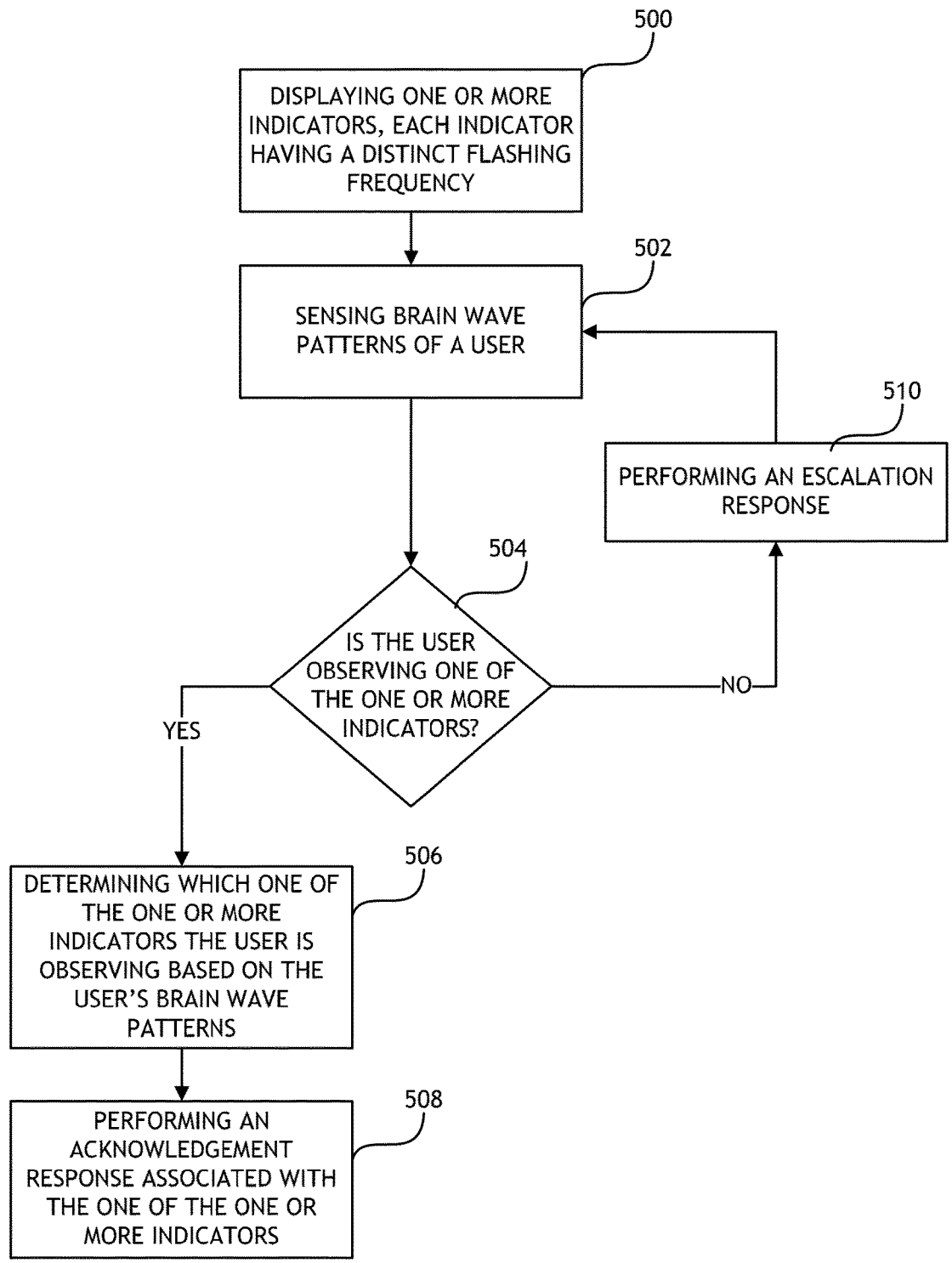
FIG. 5 shows a flowchart of another embodiment of the present invention for acknowledging a warning indicator.

Referring to FIG. 5, another embodiment of the present invention is a method for acknowledging one or more warning indicators. The method may include displaying 500 one or more flashing indicators, each flashing indicator having a distinct flashing frequency. Each distinct flashing frequency may produce distinct brain wave patterns when observed by a user. A sensor, such as an EEG, may then sense 502 the brain wave patterns of the user. If a processor determines 504, based on the user's brain wave patterns, that the user is observing one of the one or more flashing indicators, the processor may then determine 506 which of the one or more flashing indicators the user is observing. The processor may then perform 508 an acknowledgment response associated with the flashing indicator observed by the user. Such acknowledgment response may include logging the user's acknowledgment, beginning a resolution response associated with the issue indicated by the flashing indicator, reducing the prominence of the flashing indicator or any other appropriate response.

If the processor determines 504 that the user has not observed one or more of the one or more flashing indicators, the processor may perform 510 an escalation response and continue sensing 502 the user's brain wave patterns. An escalation response may include increasing the intrusiveness of the flashing indicator, delivering an audible warning, or any other appropriate response. The escalation response may include tracking the level of escalation necessary to attract the user's observation.

Figure 6:
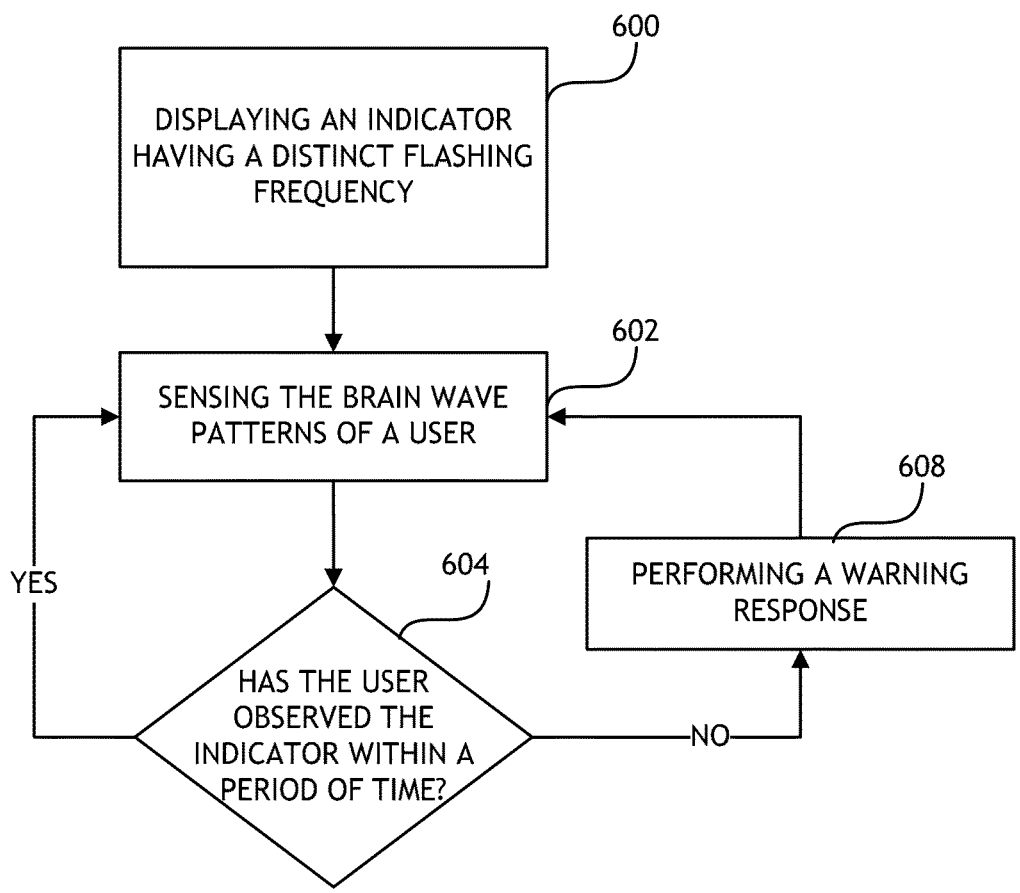
FIG. 6 shows a flowchart of another embodiment of the present invention for monitoring the alertness of a user with a flashing indicator.

Referring to FIG. 6, another embodiment of the present invention is a method for monitoring the alertness of a user. The method may include displaying 600 a flashing indicator having a distinct flashing frequency. An EEG sensor may sense 602 the brain wave patterns of a user. A processor may determine 604, based on the user's brain wave patterns, whether the user has observed the flashing indicator within a predetermined period of time. If the user has observed the flashing indicator, the processor may continue to monitor the user's brain wave patterns. If the processor determines 604 that the user has not observed the flashing indicator within the predetermined period of time, the processor may perform a warning response to warn the user that the user may not be alert. The processor may then continue to monitor the user's brain wave patterns.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. An apparatus for acknowledging an indicator comprising:
   a processor;
   memory connected to the processor that stores computer executable code;
   a display connected to the processor that displays one or more indicators, the display device comprising a heads-up display (HUD); and an electro-encephalography sensor connected to the processor that senses brain wave patterns, wherein the electro-encephalography sensor is configured to sense electrical activity in a midline occipital region of a user's brain, wherein the computer executable code is configured to:

display two or more flashing indicators, each having a flashing frequency consciously imperceptible to the user, and each flashing frequency being distinct from any other flashing indicator flashing frequency, a first flashing indicator of the two or more flashing indicators comprising a textual flashing indicator associated with a warning state, a second flashing indicator of the two or more flashing indicators is a continuously flashing indicator incorporated into a speedometer in a vehicle;

receive data measuring one or more brain wave patterns from the electro-encephalography sensor, wherein at least one of the one or more brain wave patterns are associated with the midline occipital region of the user's brain;

interpret the data measuring one or more brain wave patterns to determine if the user has observed one of the two or more flashing indicators;

determine that the user has observed the first flashing indicator based on the interpreted data measuring the one or more brain wave patterns caused by the user observing the flashing frequency of the first flashing indicator;

reduce a prominence of the first flashing indicator in response to the determination that the user has observed the first flashing indicator based on the interpreted data measuring the one or more brain wave patterns;

execute a predetermined issue resolution response associated with an issue indicated by the first flashing indicator in response to the determination that the user has observed the first flashing indicator based on the interpreted data measuring the one or more brain wave patterns;

determine that the user has not observed the second flashing indicator and speedometer for a predetermined period of time based on the interpreted data measuring the one or more brain wave patterns;

perform one or more escalation responses associated with the second flashing indicator, wherein performance of the one or more escalation responses associated with the unobserved second flashing indicator includes delivery of an audible warning;

track a level of escalation necessary to attract the user's conscious observation; and monitor the user's alertness based on the interpreted data measuring the one or more brain wave patterns.

2. The apparatus of claim 1, wherein the electro-encephalography sensor is integrated into a helmet.

3. The apparatus of claim 1, wherein the computer executable code is further configured to perform one or more acknowledgment responses when the processor determines that the user has observed the first flashing indicator.

4. The apparatus of claim 1, wherein the computer executable code is further configured to perform one or more additional escalation responses until the user observes the second flashing indicator.

5. A method for determining that a user has observed an indicator comprising:

displaying at least two flashing indicators on a heads-up display (HUD), each flashing indicator having a distinct flashing frequency consciously imperceptible to a user, at least one flashing indicator of the at least two flashing indicators incorporated into a speedometer in a vehicle;

sensing, by at least one electro-encephalography sensor configured to sense electrical activity in a midline occipital region of the user's brain, brain wave patterns of the user observing at least one of the at least two flashing indicators, wherein at least some of the brain wave patterns are associated with the midline occipital region of the user's brain;

determining which of the at least two flashing indicators the user is observing based on the brain wave patterns caused by the user observing one of the at least two flashing indicators;

reducing a prominence of the observed flashing indicator in response to the determination that the user is observing the observed flashing indicator based on the brain wave patterns;

executing a predetermined issue resolution response associated with an issue indicated by the observed flashing indicator in response to the determination that the user is observing the observed flashing indicator based on the brain wave patterns;

performing one or more escalation responses associated with unobserved flashing indicators of the at least two flashing indicators, wherein performing the one or more escalation responses associated with the unobserved flashing indicators includes delivering an audible warning;

tracking a level of escalation necessary to attract the user's conscious observation;

applying the tracked level of escalation to subsequent flashing indicators; and continuously tracking a duration of time between observations of the speedometer via the at least one flashing indicator incorporated into the speedometer.

6. The method of claim 5, wherein each of the at least two flashing indicators has a flashing frequency differentiated from the flashing frequency of every other of the at least two flashing indicators by at least 0.25 hertz.

7. The method of claim 5, further comprising performing one or more acknowledgment responses when the user has observed one of the at least two flashing indicators.

8. The method of claim 7, wherein the one or more acknowledgement responses comprise removing one of the one or more at least two flashing indicators.

9. A method for monitoring alertness of a user comprising:

continuously displaying an indicator on a heads-up display (HUD) device, the indicator having a distinct flashing frequency consciously imperceptible to the user, the indicator incorporated into a speedometer in a vehicle;

sensing, by at least one electro-encephalography sensor configured to sense electrical activity in a midline occipital region of the user's brain, brain wave patterns of the user, wherein at least some of the brain wave patterns are associated with the midline occipital region of the user's brain;

determining that the user has failed to observe the indicator for a predetermined period of time based on the brain wave patterns;

performing one or more escalation responses upon the determination that the user has failed to observe the indicator for the predetermined period of time based on the brain wave patterns, the escalation response indicating that the user has not observed the indicator of the speedometer for the predetermined period of time, wherein performing the one or more escalation responses includes delivering an audible warning;
subsequently determining that the user has observed the indicator and the speedometer based on the brain wave patterns;
tracking a level of escalation necessary to attract the user's conscious observation;
reducing a prominence of the observed indicator in response to the determination that that the user has observed the indicator and the speedometer based on the brain wave patterns; and
applying the tracked level of escalation to subsequent flashing indicators.

\* \* \* \* \*